United States Patent [19]

Miyada et al.

[11] Patent Number: 5,525,717
[45] Date of Patent: * Jun. 11, 1996

[54] SUPPORT-BOUND NUCLETIDE PROBE FOR *NEISSERIA GONORRHOEAE*

[75] Inventors: Charles G. Miyada, Mountain View; Teresa L. Born, Los Angeles, both of Calif.

[73] Assignee: Behringwerke AG, Marburg, Germany

[*] Notice: The portion of the term of this patent subsequent to Oct. 26, 2010, has been disclaimed.

[21] Appl. No.: 83,946

[22] Filed: Jun. 25, 1993

Related U.S. Application Data

[62] Division of Ser. No. 611,528, Nov. 9, 1990, Pat. No. 5,256,536.

[51] Int. Cl.$^6$ .............................. C07H 21/00; C12Q 1/68; C12P 19/34
[52] U.S. Cl. .................... 536/24.32; 536/24.3; 536/23.1; 435/6; 435/91.1; 435/871
[58] Field of Search ............................. 435/6, 91.1, 871; 536/23.1, 24.3, 24.32; 422/55, 56, 67, 68.1

[56] References Cited

U.S. PATENT DOCUMENTS

| | | | |
|---|---|---|---|
| 4,358,535 | 11/1982 | Falkow et al. | 435/5 |
| 4,446,230 | 5/1984 | Zubrxycki | 435/6 |
| 4,755,458 | 7/1988 | Rabbani et al. | 435/5 |
| 4,795,562 | 1/1989 | Walsh | 210/232 |
| 4,812,216 | 3/1989 | Hurd et al. | 204/182.8 |
| 4,818,680 | 4/1989 | Collins et al. | 435/6 |
| 4,849,078 | 7/1989 | Love et al. | 204/182.8 |
| 4,900,659 | 2/1990 | Lo et al. | 435/6 |
| 5,047,523 | 9/1991 | Woods et al. | 536/27 |
| 5,099,011 | 3/1992 | Woods et al. | 536/27 |
| 5,162,199 | 11/1992 | Stern et al. | 435/6 |
| 5,256,536 | 10/1993 | Miyada et al. | 435/6 |

FOREIGN PATENT DOCUMENTS

| | | |
|---|---|---|
| 0227976A2 | 7/1987 | European Pat. Off. . |
| 0337896A1 | 10/1989 | European Pat. Off. . |
| 0337896 | 10/1989 | European Pat. Off. .......... C12Q 1/68 |
| WO88/03957 | 6/1988 | WIPO . |

OTHER PUBLICATIONS

Welcher, et al., "Selective enrichment of specific DNA, cDNA and RNA sequences using biotinylated probes, avidin and copper–chelate agarose" *Nucleic Acids Research*, vol. 14:24, pp. 10027–10044 (1986).
Perry, et al. "Structural analysis of the pi/E region of *Neisseria gonorrhoeae* P9" *Gene*, vol. 60, pp. 85–92 (1987).
Donegan, et al., "Isolation of a species–specific DNA probe *Neisseria gonorrhoeae* using a novel technique particularly suitable for use with closely related species displaying high levels of DNA homology" *Moleclar and Cellular Probes*, vol. 3, pp. 13–26 (1989).
Totten, et al., "DNA Hybridization Technique for the Detection of *Neisseria gonorrheae* in Men with Urethritis" *The Journal of Infectious Diseases*, vol. 148:3, pp. 462–471 (Sep. 1983).
Kuritza, et al., "Identification of *Neisseria gonorrhoeae* with the ORTHOProbe DNA Probe Test" *Diagnostic Microbiology and Infectious Diseases*, vol. 12, pp. 129–132 (1989).
Kolberg, et al. "The specificity of pillin DNA sequences for detection of pathogenic Neisseria" *Molecular and Cellualr Probes*, vol. 3, pp. 59–72 (1989).
Granato, et al., "Evaluation of Prototype DNA Probe Test for the Noncultural Diagnosis of Gonnorrhea" *Journal of Clinical Microbiology*, vol. 27:4, pp. 632–635 (Apr. 1989).
Knapp, "Historical Perspectives and Identification of Neisseria and Related Species" *Clinical Microbiology Reviews*, vol. 1:4, pp 415–431 Oct. 1988.
Torres, et al.,"Differentiation of *Neisseria Gonorrhoeae* from other Neisseria Species by Use of the Restriction Endonuclease *Hea*III" *Journal of Clinical Microbiology*, vol. 20:4, pp. 687–690 (Oct. 1984).
Pollice, et al., "Use of Nonradioactive DNA Probes for the Detection of Infectious Bacteria" *Clinics in Laboratory Medicine*, vol. 5:30, pp. 463–473 (Sep.1985).
Stern, et al., "Opacity Genes in *Neisseria gonorrhoeae*: Control of Phase and Antigenic Variation" *Cell*, vol. 47, pp. 61–71 (Oct. 10, 1986).
Stern, et al., "Opacity Determinants of *Neisseria gonorrhoeae*: Gene Expression and Chromosomal Linkage to the Gonococcal Pilus Gene" *Cell*, vol. 37, pp. 447–456 (Jun. 1984).
Halter, et al., "IgA protease of *Neisseria gonorrhoeae*: Isolation and characterization of the gene and its extracellular product" *The EMBO Journal*, vol. 3:7, pp. 1595–1601 (1984).
Haas, et al., "The Repertoire of Silent Pilus Genes in *Neisseria gonorrhoeae*: Evidence for Gene Conversion" *Cell*, vol. 44, pp. 107–115 (Jan. 17, 1986).
Miyada, et al., "A DNA sequence for the discrimination of *Neisseria gonorrhoeae* from other Neisseria species" *Molecular and Cellular Probes*, vol. 5, pp. 327–335 (1991).

*Primary Examiner*—W. Gary Jones
*Assistant Examiner*—David Schreiber
*Attorney, Agent, or Firm*—Shelley G. Precivale; Theodore J. Leitereg

[57] ABSTRACT

A nucleotide sequence characteristic of *Neisseria gonorrhoeae* is disclosed. The sequence can be the basis for hybridization type, nucleic acid-based, rapid, in vitro diagnostic assays. The unique nature of the sequence makes it possible to clearly discriminate *N. gonorrhoeae* from other Neisseria species thus eliminating or substantially reducing the number of false positive readings. A 350 base pair *N. gonorrhoeae* DNA restriction fragment was cloned after subtractive hybridization to *Neisseria meningitidis* DNA. In further cloning experiments the sequences adjacent to the original 350 base pair fragment were determined. A portion of this sequence was shown to detect 105 of 106 *N. gonorrhoeae* strains and no other Neisseria species. In addition to use as detection probes, all or portions of the nucleotide sequence can be used as a ligand for the sandwich capture of *N. gonorrhoeae* sequences and as primers for in vitro amplification of *N. gonorrhoeae* sequences. The polypeptides encoded by the presently disclosed sequence, including antibodies thereto, are also disclosed as are their uses.

1 Claim, 2 Drawing Sheets

```
AspProThrIleProAspCysAspIleIleLeuGlyGlyPheProCysGlnAspPheSer
GATCCAACTATTCCCGATTGCGACATCATTTTAGGCGGATTCCCTTGTCAAGATTTTTCC    60

MetIleTrpLysGlnProGlyLeuGluGlyGluArgGlyAsnLeuTyrLysSerPheLeu
ATGATTTGGAAACAGCCGGGCTTAGAGGGTGAGCGCGGCAATCTTTATAAAAGCTTTTTA  120

ArgPheValAsnAlaLysLysProLysValPheValAlaGluAsnValLysGlyLeuLeu
CGTTTTGTAAATGCAAAAAAACCGAAAGTTTTTGTTGCTGAGAATGTGAAAGGTTTATTG  180

ThrAlaAsnLysLysLysAlaIleGlnGlnIleIleThrAspPheGluAsnCysGlyTyr
ACTGCCAACAAGAAAAAAGCCATCCAGCAAATTATTACCGACTTTGAAAATTGCGGTTAT  240

TyrValGlnAlaLysLeuTyrAsnPheAlaGluPheGlyValProGlnPheArgGluArg
TACGTTCAGGCGAAGCTGTATAACTTTGCAGAATTTGGCGTACCTCAATTTCGTGAACGT  300

ValLeuIleValGlyValArgLeuAspThrGlyPheAspPheArgHisProGluProThr
GTGCTGATTGTCGGAGTACGTTTGGATACAGGATTTGATTTTCGCCATCCGGAACCGACG  360

HisAsnGluThrGlyGluAsnGlyLeuLysProTyrValThrAlaGlyGlnAlaIleSer
CACAATGAAACTGGCGAAAACGGCTTAAAACCATATGTAACAGCAGGTCAGGCCATATCC  420

AsnIleProGlnAsnAlaSerAsnAsnGluLeuLeuLysIleSerGlyLysThrArgArg
AATATTCCACAAAATGCCAGTAATAATGAATTACTGAAAATCAGCGGTAAAACACGCCGT  480

MetLeuGluLeuIleProGluGlyGlyAsnPheThrAspIleProLysAspHisProLeu
ATGTTCGAATTAATTCCTGAAGGTGGAAATTTTACCGATATTCCTAAAGATCATCCTTTA  540

TyrValLysGlyMetIleSerHisValTyrArgArgMetHisArgAsnGluProSerLys
TATGTGAAAGGTATGATTAGCCACGTTTATCGTCGTATGCATCGGAACGAGCCATCAAAA  600

ThrIleIleAlaAlaGlyGlyGlyGlyThrTrpAlaIleThrSerLeuAsnArgValLeu
ACAATTATTGCAGCAGGTGGCGGTGGTACTTGGGCTATCACTTCCCTGAACCGCGTGCTT  660

LeuLeuIleGluAsnGluGlnGlyPheLysValPheLeuMetIleLeuSerLeuSerAsp
TTACTAATAGAGAACGAGCAAGGCTTCAAAGTTTTCCTGATGATTTTGAGTTTGTCGGAT  720

GlnGlnLeuLysTyrValAlaArgLeuValMetLeuPheLeuLeuArgAlaTrpLeuAsn
CAACAACTGAAGTACGTCGCCAGATTGGTAATGCTGTTCCTCCTCAGGGCGTGGTTGAAC  780

TrpGlnLysAlaPheTyrArgPhePheGlnThrThrMetArgLysEnd
TGGCAAAAAGCATTTTACCGATTTTTTCAGACAACTATGAGAAAGTAGATTTGCATGAGA  840

AATTAGTCGA  850
```

*FIG._1*

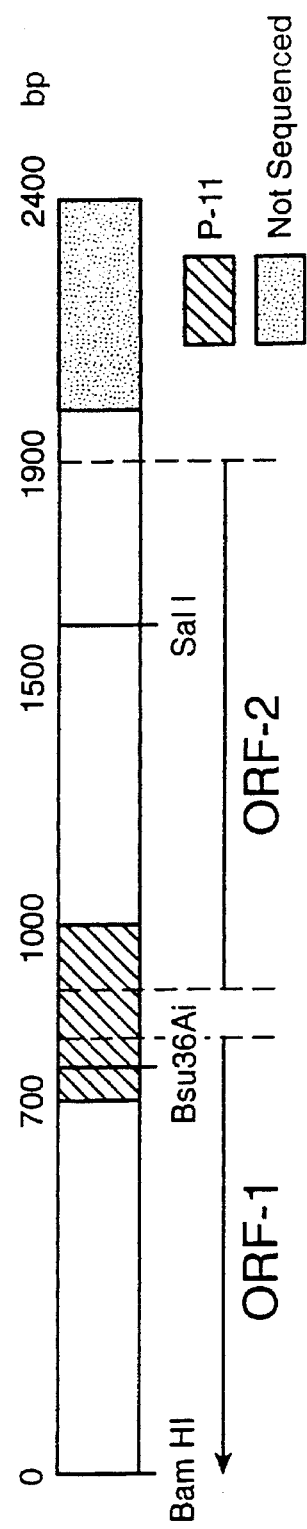
FIG._2

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 850 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( v i ) ORIGINAL SOURCE:
    ( A ) ORGANISM: Neisseria gonorrheae
    ( B ) STRAIN: Strain #125

( x i ) SEQUENCE DESCRIPTION: SEQ ID NO:1:

| | | | | | | |
|---|---|---|---|---|---|---|
| GATCCAACTA | TTCCCGATTG | CGACATCATT | TTAGGCGGAT | TCCCTTGTCA | AGATTTTTCC | 60 |
| ATGATTTGGA | AACAGCCGGG | CTTAGAGGGT | GAGCGCGGCA | ATCTTTATAA | AAGCTTTTTA | 120 |
| CGTTTTGTAA | ATGCAAAAAA | ACCGAAAGTT | TTTGTTGCTG | AGAATGTGAA | AGGTTTATTG | 180 |
| ACTGCCAACA | AGAAAAAAGC | CATCCAGCAA | ATTATTACCG | ACTTTGAAAA | TTGCGGTTAT | 240 |
| TACGTTCAGG | CGAAGCTGTA | TAACTTTGCA | GAATTTGGCG | TACCTCAATT | TCGTGAACGT | 300 |
| GTGCTGATTG | TCGGAGTACG | TTTGGATACA | GGATTTGATT | TTCGCCATCC | GGAACCGACG | 360 |
| CACAATGAAA | CTGGCGAAAA | CGGCTTAAAA | CCATATGTAA | CAGCAGGTCA | GGCCATATCC | 420 |
| AATATTCCAC | AAAATGCCAG | TAATAATGAA | TTACTGAAAA | TCAGCGGTAA | AACACGCCGT | 480 |
| ATGTTCGAAT | TAATTCCTGA | AGGTGGAAAT | TTTACCGATA | TTCCTAAAGA | TCATCCTTTA | 540 |
| TATGTGAAAG | GTATGATTAG | CCACGTTTAT | CGTCGTATGC | ATCGGAACGA | GCCATCAAAA | 600 |
| ACAATTATTG | CAGCAGGTGG | CGGTGGTACT | TGGGCTATCA | CTTCCCTGAA | CCGCGTGCTT | 660 |
| TTACTAATAG | AGAACGAGCA | AGGCTTCAAA | GTTTCCTGA | TGATTTGAG | TTTGTCGGAT | 720 |
| CAACAACTGA | AGTACGTCGC | CAGATTGGTA | ATGCTGTTCC | TCCTCAGGGC | GTGGTTGAAC | 780 |
| TGGCAAAAAG | CATTTTACCG | ATTTTTTCAG | ACAACTATGA | GAAAGTAGAT | TTGCATGAGA | 840 |
| AATTAGTCGA | | | | | | 850 |

( 2 ) INFORMATION FOR SEQ ID NO:2:

( i ) SEQUENCE CHARACTERISTICS:
    ( A ) LENGTH: 275 amino acids
    ( B ) TYPE: amino acid (C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:
(A) ORGANISM: Neisseria gonorrheae
(B) STRAIN: Strain #125

(xi) SEQUENCE DESCRIPTION: SEQ ID NO:2:

```
Asp Pro Thr Ile Pro Asp Cys Asp Ile Ile Leu Gly Gly Phe Pro Cys
1               5                   10                  15
Gln Asp Phe Ser Met Ile Trp Lys Gln Pro Gly Leu Glu Gly Glu Arg
            20                  25                  30
Gly Asn Leu Tyr Lys Ser Phe Leu Arg Phe Val Asn Ala Lys Lys Pro
            35                  40                  45
Lys Val Phe Val Ala Glu Asn Val Lys Gly Leu Leu Thr Ala Asn Lys
        50                  55                  60
Lys Lys Ala Ile Gln Gln Ile Ile Thr Asp Phe Glu Asn Cys Gly Tyr
65                  70                  75                  80
Tyr Val Gln Ala Lys Leu Tyr Asn Phe Ala Glu Phe Gly Val Pro Gln
                85                  90                  95
Phe Arg Glu Arg Val Leu Ile Val Gly Val Arg Leu Asp Thr Gly Phe
            100                 105                 110
Asp Phe Arg His Pro Glu Pro Thr His Asn Glu Thr Gly Glu Asn Gly
            115                 120                 125
Leu Lys Pro Tyr Val Thr Ala Gly Gln Ala Ile Ser Asn Ile Pro Gln
    130                 135                 140
Asn Ala Ser Asn Asn Glu Leu Leu Lys Ile Ser Gly Lys Thr Arg Arg
145                 150                 155                 160
Met Leu Glu Leu Ile Pro Glu Gly Gly Asn Phe Thr Asp Ile Pro Lys
                165                 170                 175
Asp His Pro Leu Tyr Val Lys Gly Met Ile Ser His Val Tyr Arg Arg
            180                 185                 190
Met His Arg Asn Glu Pro Ser Lys Thr Ile Ile Ala Ala Gly Gly Gly
            195                 200                 205
Gly Thr Trp Ala Ile Thr Ser Leu Asn Arg Val Leu Leu Leu Ile Glu
    210                 215                 220
Asn Glu Gln Gly Phe Lys Val Phe Leu Met Ile Leu Ser Leu Ser Asp
225                 230                 235                 240
Gln Gln Leu Lys Tyr Val Ala Arg Leu Val Met Leu Phe Leu Leu Arg
                245                 250                 255
Ala Trp Leu Asn Trp Gln Lys Ala Phe Tyr Arg Phe Phe Gln Thr Thr
            260                 265                 270
Met Arg Lys
    275
```

(2) INFORMATION FOR SEQ ID NO:3:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( v i ) ORIGINAL SOURCE:
    ( A ) ORGANISM: Neisseria gonorrheae
    ( B ) STRAIN: Strain #125

( x i ) SEQUENCE DESCRIPTION: SEQ ID NO:3:

```
ACAGCATTAC CAATCTGGCG                                                    20
```

( 2 ) INFORMATION FOR SEQ ID NO:4:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Neisseria gonorrheae
        ( B ) STRAIN: Strain #125

( x i ) SEQUENCE DESCRIPTION: SEQ ID NO:4:

```
GATCCAACTA TTCCCGATTG CGACATCATT TTAGGCGGAT TCCCTTGTCA AGATTTTCC         60
ATGATTTGGA AACAGCCGGG CTTAGAGGGT GAGCGCGGCA ATCTTTATAA AAGCTTTTTA       120
CGTTTTGTAA ATGCAAAAAA ACCGAAAGTT TTTGTTGCTG AGAATGTGAA AGGTTTATTG       180
ACTGCCAACA AGAAAAAAGC CATCCAGCAA ATTATTACCG ACTTTGAAAA TTGCGGTTAT       240
TACGTTCAGG CGAAGCTGTA TAACTTTGCA GAATTT                                 276
```

( 2 ) INFORMATION FOR SEQ ID NO:5:

( i ) SEQUENCE CHARACTERISTICS:
        ( A ) LENGTH: 303 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Neisseria gonorrheae
        ( B ) STRAIN: Strain #125

( x i ) SEQUENCE DESCRIPTION: SEQ ID NO:5:

```
AACTTTGCAG AATTTGGCGT ACCTCAATTT CGTGAACGTG TGCTGATTGT CGGAGTACGT        60
TTGGATACAG GATTTGATTT TCGCCATCCG GAACCGACGC ACAATGAAAC TGGCGAAAAC       120
GGCTTAAAAC CATATGTAAC AGCAGGTCAG GCCATATCCA ATATTCCACA AAATGCCAGT       180
AATAATGAAT TACTGAAAAT CAGCGGTAAA ACACGCCGTA TGTTCGAATT AATTCCTGAA       240
```

```
GGTGGAAATT  TTACCGATAT  TCCTAAAGAT  CATCCTTTAT  ATGTGAAAGG  TATGATTAGC       300

CAC                                                                          303
```

( 2 ) INFORMATION FOR SEQ ID NO:6:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Neisseria gonorrheae
        ( B ) STRAIN: Strain #125

( x i ) SEQUENCE DESCRIPTION: SEQ ID NO:6:

```
GTATGATTAG  CCACGTTTAT  CGTCGTATGC  ATCGGAACGA  GCCATCAAAA  ACAATTATTG        60

CAGCAGGTGG  CGGTGGTACT  TGGGCTATCA  CTTCCCTGAA  CCGCGTGCTT  TTACTAATAG       120

AGAACGAGCA  AGGCTTCAAA  GTTTTCCTGA  TGATTTTGAG  TTTGTCGGAT  CAACAACTGA       180

AGTACGTCGC  CAGATTGGTA  ATGCTGTTCC  TCCTCAGGGC  GTGGTTGAAC  TGGCAAAAAG       240

CATTTTACCG  ATTTTTTCAG  ACAACTATGA  GAAAGTAGAT  TTGCATGAGA  AATTAGTCGA       300
```

SUPPORT-BOUND NUCLETIDE PROBE FOR *NEISSERIA GONORRHOEAE*

This is a division of application Ser. No. 07/611,528, filed on Nov. 9, 1990, now issued as U.S. Pat. No. 5,256,536.

BACKGROUND OF THE INVENTION

FIELD OF THE INVENTION

Nucleic acid hybridization is an excellent tool to identify nucleic acids, and is based upon the principle of complementary base pairing. When single stranded nucleic acids are incubated in solution, complementary base sequences pair to form double-stranded stable hybrid molecules, referred to as DNA complexes. The ability of single-stranded deoxyribonucleic acid (DNA) or ribonucleic acid (RNA) to form a hydrogen bonded structure with its complementary nucleotide sequence is often utilized as an analytical tool in recombinant DNA research to identify, isolate and characterize various nucleotide sequences of biological interest.

Detection of gonorrhea is one area in which nucleic acid hybridization holds great potential as a diagnostic tool in clinical medicine. Use of nucleotide probes provides an alternative diagnostic method that can potentially eliminate culturing while simultaneously increase the sensitivity and specificity of an assay for the detection of gonorrhea.

Gonorrhea is one of the most commonly reported bacterial infections. The causative agent, *Neisseria gonorrhoeae*, is typically identified by culturing on selective agar medium, gram-staining, and cytochrome oxidase and carbohydrate utilization testing. Knapp, *Clinical Microbiology Review* (1988) 1(4):415–431. U.S. Pat. No. 4,446,230 discloses use of a novel test strain of *N. gonorrhoeae* in culture detection of *N. gonorrhoeae* DNA. These tests are usually sufficient to discriminate *N. gonorrhoeae* from other Neisseria species.

Commercial serological assays, including coagglutination and fluorescent antibody staining, have also been described for the identification of *N. gonorrhoea*. Knapp, supra.

This invention relates to novel nucleotide sequences and hybridization procedures for using these sequences. And in particular, this invention relates to nucleotide sequences that are specific for *Neisseria gonorrhoeae*.

DESCRIPTION OF THE RELATED ART

Several DNA probe systems have been described for the rapid identification of *N. gonorrhoeae*. Common to these systems is the use of a nucleotide sequence that is unique to the species *N. gonorrhoeae*, yet is also capable of recognizing many of its serotypes. A problem in obtaining species-specific probes is overcoming potential cross-hybridization to closely related species. This often requires initial removal of sequences that have homology to the closely related species. There are two subtractive hybridization strategies that have been utilized to enrich for sequences nonhomologous to *N. meningitidis* in order to isolate the *N. gonorrhoeae* specific probes. See Welcher et al., *Nucleic Acids Research* (1986) 14(24):10027–10044 and Donegan et al., *Molecular and Cellular Probes* (1989) 3:13–26.

Use of a radiolabeled gonococcal cryptic plasmid sequence has been shown to detect 87% of culture-positive *N. gonorrhoeae* cases. Totten, et al., *Journal of Infectious Diseases* (1983) 148(3):462–471. These probes are only capable of detecting strains of *N. gonorrhoeae* which contain plasmid DNA.

Nonradioactive DNA probes have been developed to detect infectious bacteria such as *N. gonorrhoeae*, Pollice et al., *Clinics in Laboratory Medicine* (1985) 5(3):463–473. In particular, a biotinylated DNA probe assay for the culture confirmation of *N. gonorrhoeae* strains is described in Kuritza et al., *Diagnostic Microbiology and Infectious Diseases* (1989) 12:129–132.

Additionally, nucleic acid probe assays for the noncultural diagnosis of gonorrhea have been developed, such as is described in Kolberg et al., *Molecular and Cellular Probes* (1989) 3:59–72 which pertains to an assay based upon the DNA sequence of the pilin gene. WO-88/03957 pertains to a nucleic acid probe assay based upon a ribosomal RNA sequence. See also Granato et al., *Journal of Clinical Microbiology* (1989) 27(4):632–635.

U.S. Pat. No. 4,755,458 discloses the use of a recombinant plasmid consisting of a DNA fragment from *N. gonorrhoeae* cloned into the vector pBR322, to detect *N. gonorrhoeae* DNA. The reference generally pertains to a method of detecting polynucleotide sequences.

U.S. Pat. No. 4,900,659 pertains to polynucleotide probe compositions that are capable of hybridizing to *N. gonorrhoeae* chromosomal DNA. The compositions are obtained from ATCC strains of *N. gonorrhoeae*.

EP 337896 discloses specific nucleotide sequences useful as probes in detecting Neisseria strains. More generically, EP 227976 pertains to nucleotide probes useful in detecting human infectious diseases such as gonorrhea.

SUMMARY OF THE INVENTION

The invention disclosed herein pertains to a novel sequence of nucleotides specific for *Neisseria gonorrhoeae*, and fragments thereof. In particular, this invention includes methods and compositions for determining the presence of a gonorrhea infection. This involves determining the presence of *N. gonorrhoeae* nucleic acids in a sample suspected of being infected with gonorrhea. The method comprises using at least one polynucleotide probe specific for *N. gonorrhoeae* which is capable of selectively hybridizing to the DNA sequence of FIG. 1 or its complement. A typical probe of this invention comprises about seventeen or more nucleotides, preferably twenty or more. A medium suspected of containing *N. gonorrhoeae* nucleic acids is combined with the probe under conditions which allow the probe to hybridize to any single stranded *N. gonorrhoeae* nucleic acids present in the sample to form complexes, such as DNA complexes. The "medium" can be any solution or carrier suspected of containing an infectious organism or any antigen derived from said organism, and includes patient samples such as urine, plasma or other bodily fluids or secretions.

The method further includes detecting the complexes as an indication of the presence of gonorrhea infection in the sample. Detection can be accomplished by labeling the probe with a radioactive isotope or an enzyme, for example.

The polynucleotide probe of this invention comprises at least seventeen, usually at least twenty nucleotides capable of hybridizing to the DNA sequence of FIG. 1 or its complement. In one embodiment, the probe is capable of hybridizing to at least seventeen effectively contiguous nucleotides in the DNA sequence of FIG. 1 or its complement. In another embodiment, the probe comprises at least seventeen effectively contiguous nucleotides. In a still further embodiment, the probe comprises at least seventeen effectively contiguous nucleotides and is capable of hybridizing to at least seventeen effectively contiguous nucleotides in the DNA sequence of FIG. 1 or its complement. In any of these embodiments, the hybridized regions of the probe and the DNA sequence of FIG. 1 or its complement, usually have 90–100% complementarity.

The invention also includes kits containing in a packaged combination the materials for carrying out the assay.

An advantage of the present invention is that the methods, materials and kits provide a high degree of accuracy with respect to the detection of *N. gonorrhoeae* nucleic acids with substantial minimization or virtual elimination of false positive readings. By using several different probes, greater sensitivity of the assay can be achieved. This is due to the fact that each probe would hybridize to a different area of the *N. gonorrhoeae* nucleic acid, so that if each probe was labeled, the analyte would bear multiple labels. A feature of the present invention is that the nucleotide sequences disclosed can be readily used with conventional assay devices and hybridization procedures to provide improved accuracy in gonorrhea detection.

These and other objects, advantages and features of the present invention will become apparent to those persons skilled in the art upon reading the details of the invention as more fully set forth below.

BRIEF DESCRIPTION OF THE DRAWING

FIG. 1 depicts a nucleotide sequence specific for *N. gonorrhoeae* (SEQ ID NO:1) and its deduced amino acid sequence (SEQ ID NO:2).

FIG. 2 depicts the restriction map of the plasmid GC-24 which hybridizes to the P-11 riboprobe.

DESCRIPTION OF THE SPECIFIC EMBODIMENTS

Before proceeding further with a description of the specific embodiments of the present invention, a number of terms will be defined.

Analyte: *N. gonorrhoeae* nucleic acids which are detected in order to ascertain whether a sample is infected with gonorrhea. The nucleic acids can be from any source in purified or unpurified form, including without limitation, DNA (dsDNA and ssDNA) and RNA, including tRNA, mRNA, rRNA, DNA-RNA hybrids, or mixtures thereof, genes, chromosomes and plasmids. The sample can be pre-treated for example, so that the analyte is cleaved to obtain a fragment that contains a target polynucleotide sequence ("target sequence"). Cleavage can be accomplished in numerous ways, for example, by shearing or by treatment with an endonuclease such as a restriction endonuclease or other site specific chemical cleavage method. For purposes of this invention the analyte will usually be at least partially denatured or single-stranded or treated to render it denatured or single-stranded. Such treatments are well known in the art and include, for instance, heat or alkali treatment. For example, double stranded DNA can be heated at 90°–100° C. for a period of about 1 to 10 minutes to produce denatured material.

Polynucleotide probe: a probe usually a DNA probe, capable of hybridizing with the single stranded analyte. In addition, the probe is capable of being detected. Thus, the probe generally consists of two parts. One part of the probe is capable of hybridizing with the analyte. The other part of the probe includes a portion that renders the probe capable of being detected. Generally, a conjugate suitable for use in this invention comprises the probe and a label capable of producing a detectable signal either alone or by interaction with other members of a signal producing system. The label can initially be a part of or bound to the probe or the label can bind to the probe during or after hybridization to the analyte. In the latter case, a specific binding pair member ("sbp member"), such as a specific polynucleotide sequence or a hapten, can be bound to the probe and the label can be bound to a complementary sbp member. Exemplary of such sbp members and their complementary sbp members are ligands and receptors, antigens and antibodies, haptens and antibodies, biotin and avidin, an oligonucleotide and complementary oligonucleotide, an operon and its repressor, DNA-RNA heteroduplex and antibodies thereto and the like. Delaying the binding of the label to the polynucleotide probe as described above offers an advantage when hybridization of the probe and analyte would be impeded by the presence of the label or when the label is unstable or insoluble under the hybridization conditions.

Member of a specific binding pair ("sbp member"): one of two different molecules, having an area on the surface or in a cavity which specifically binds to and is thereby defined as complementary with a particular spatial and polar organization of the other molecule. The members of a specific binding pair are referred to as ligand and receptor (antiligand). These are usually members of an immunological pair such as an antigen and an antibody. However, specific binding pairs which are not immunological pairs are also included in the scope of this invention. These include: organic residues having a molecular weight of about 125–1500 and receptors for said residues, for example, biotin and avidin; hormones and hormone receptors; nucleic acid duplexes; IgG and protein A; DNA-DNA; DNA-RNA; and the like. Sbp members may be part of the support means and/or part of the labeling means.

Ligand: any organic compound for which a receptor naturally exists or can be prepared.

Receptor ("antiligand"): any compound or composition capable of recognizing a particular spatial and polar organization of a molecule, e.g., epitopic or determinant site. Typical receptors include naturally occurring receptors, e.g., thyroxine binding globulin, antibodies, enzymes, Fab fragments, lectins, nucleic acids, protein A, complement component Clq, and the like.

Small organic molecule: a compound having a molecular weight of less than 1500, preferably 100 to 1000 and more preferably between the range of 300 to 600 such as biotin, fluorescein, rhodamine and other dyes, tetracycline and other protein binding molecules, and haptens. The small organic molecule can provide a means of attachment of a nucleotide sequence to a label or a support.

Support: a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper and chromatographic paper; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon and poly(vinyl butyrate). These materials can be used alone or in conjunction with other materials such as glass, ceramics, metals, and the like.

Binding of sbp members to the support may be accomplished by techniques which are well known in the art and adequately described in the literature. See, for example, "Immobilized Enzymes," Ichiro Chibata, Halsted Press, New York (1978) and Cuatrecasas, *Journal of Biological Chemistry* (1970) 245:3059.

Label: member of the signal producing system ("sps member") that is conjugated to or becomes bound to the polynucleotide probe. In general, any label that is detectable by virtue of its being aggregated or spacially proximate to another label can be used. The label can be isotopic or nonisotopic, usually non-isotopic, and can be a catalyst, enzyme, coenzyme, dye, fluorescer, quencher, chemiluminescer, and the like. The label can also be a particle such as latex or carbon particle, metal sols, crystallite, liposome, cell, etc. which may or may not be further labeled with a dye, catalyst or other detectible group. The label can generate a detectable signal either alone or together with other sps members. The label can be bound directly to the polynucleotide probe or can become bound indirectly to the probe, such as by being bound to an sbp member complementary to an sbp member that is bound to the probe.

Signal Producing System: The signal producing system may have one or more components, at least one component being the label. The signal producing system generates a signal that relates to the presence or amount of analyte in a sample. The signal producing system includes all of the materials required to produce a measurable signal. When the label is not conjugated to the polynucleotide probe, the label is normally bound to an sbp member complementary to an sbp member that is bound to or part of the polynucleotide probe. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. The signal producing system may also contain coenzymes, substances that react with enzymic products, other enzymes and catalysts, and the like. The signal producing system provides a signal detectable by external means, preferably by measurement of the degree of aggregation of particles or by use of electromagnetic radiation, desirably by visual examination. For the most part, the signal producing system will involve particles, such as fluorescent particles or other light absorbing particles, a chromophoric substrate and enzyme, where chromophoric substrates are enzymatically converted to dyes which absorb light in the ultraviolet or visible region, phosphors, fluorescers or chemiluminescers.

The signal producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of analyte in the sample.

A large number of enzymes and coenzymes useful in a signal producing system are indicated in U.S. Pat. No. 4,275,149, columns 19 to 23, U.S. Pat. No. 4,318,980, columns 10 to 14, and U.S. Pat. No. 4,868,104, column 7. Additionally, a number of enzyme combinations are set forth in U.S. Pat. No. 4,275,149, columns 23 to 28, which combinations are useful in the subject invention. All of the aforementioned disclosures are incorporated herein by reference.

The signal producing system can also include one or more particles, which are insoluble particles of at least about 50 nm and not more than about 50 microns in diameter. The particles may be organic or inorganic, porous or non-porous, are preferably of a density approximating water, and are composed of a material that can be transparent, partially transparent, or opaque. An excellent discussion of suitable particles is set forth in U.S. Pat. No. 4,868,104, columns 8 to 9, the disclosure of which is incorporated herein by reference.

Ancillary Materials: Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic salts such as formamide, quaternary ammonium salts, polycations such as dextran sulfate, or surfactants, particularly non-ionic surfactants, binding enhancers, e.g., polyalkylene glycols, or the like.

Hybridization (hybridizing) and specificity (specific for): in the context of nucleotide sequences these terms are used interchangeably herein. The ability of two nucleotide sequences to hybridize to each other is based on the degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like. In particular, "selective hybridization" pertains to conditions in which the degree of hybridization of the polynucleotide probe of this invention to the analyte would require complete or nearly complete complementarity. The complementarity must be sufficiently high to assure that the probe will bind specifically to the analyte relative to binding to other nucleic acids present in a sample. Namely, complementarity will be 90–100%, preferably 95–100%, most preferably 100%.

Contiguous: sequences are considered to be contiguous when two segments or two sequences of a polynucleotide are directly bonded together and thereby form a single uninterrupted sequence. This describes the situation where the hybridized portions of the analyte sequence and the polynucleotide probe have nucleotides that are contiguous. As a variation of this, the term "effectively contiguous" contemplates the situation where the sequence recognized by the probe is interrupted by nucleotides contained in looped portions that do not hybridize to the probe or where the probe has looped portions that do not hybridize with the analyte. There may also be the situation where there is substantial but not complete complementarity such that some nucleotides within the sequence are not paired with the probe.

As mentioned above, the method of the present invention allows the determination of the presence of *N. gonorrhoeae* nucleic acids in a sample suspected of being infected with gonorrhea. Gonorrhea infection can have serious medical consequences and necessary antibiotic treatment presents the risk of adverse reactions and development of antibiotic resistant strains. Any assay designed to detect the presence of the infection must further be designed so as to avoid false negative and false positive readings, i.e., avoid giving results indicating no infection when in fact an infection is present and vice versa. Accordingly, assays are preferably designed so as to detect possible infections while still obtaining a low incidence of false positive readings, i.e., results indicating an infection when in fact no infection is present. The present invention provides an assay which is highly sensitive thus substantially reducing or eliminating false negatives and highly selective thus substantially reducing or eliminating false positives.

The invention is primarily directed to unique nucleotide sequences obtained from *N. gonorrhoeae* chromosomal DNA, which provide improved sensitivity and selectivity. The entire sequence of FIG. 1 or one or more fragments comprising at least seventeen and preferably at least twenty nucleotides can be used in hybridization type, nucleic acid-based, rapid, in vitro diagnostic assays. Prior art assays provided false positive results, whereas the unique nature of the present sequences make it possible to clearly discriminate *N. gonorrhoeae* from other Neisseria thus eliminating or substantially reducing the number of false positive readings.

A major problem in obtaining a species-specific probe for *N. gonorrhoeae* is overcoming potential cross-hybridization to the closely related species, *Neisseria meningitidis*. These species are 93% homologous at the DNA level so the cloning of probes which are specific to *N. gonorrhoeae* require an initial removal of sequences that had homology to *N. meningitidis*.

A subtractive hybridization strategy was utilized to enrich for sequences nonhomologous to *N. meningitidis* in order to isolate the *N. gonorrhoeae* specific probes of the invention. The phenol-emulsion reassociation technique (PERT) was combined with DNA cloning, which is set forth in detail in Kunkel et al., *Proc. Natl. Acad. Sci. USA* (1985) 82:4778–4782. This method resulted in an insert (designated p-11) with highly desirable hybridization characteristics. Isolation of plasmids containing chromosomal regions adjacent to the P-11 led to identification of a sequence that was specific for *N. gonorrhoeae*.

The unique 850 nucleotide sequence of this invention is specific for *N. gonorrhoeae* and is shown in FIG. 1, with the corresponding amino acid protein sequence shown above it. In the nucleotide sequence, A, C, G and T stand for adenine, cytosine, guanine and thymine, respectively. In the protein sequence, standard three letter abbreviations are used for amino acids. Similarly, the sequence complementary to the sequence of FIG. 1 is also specific for *N. gonorrhoeae*. The numbers shown in FIG. 1 refer to the nucleotide position.

This invention contemplates use of probes comprising at least seventeen and preferably twenty nucleotides which hybridize to the DNA sequence of FIG. 1 or its complement, in the detection of gonorrhea infection. This unique sequence of 850 nucleotides has been shown to detect 105 of 106 strains of *N. gonorrhoeae* tested and no other Neisseria species in nucleic acid hybridization experiments.

In a broad sense, this invention contemplates use of a polynucleotide probe that is capable of selectively hybridizing to the DNA sequence of FIG. 1 or its complement. In the preferred embodiment, the polynucleotide probe comprises at least seventeen nucleotides, preferably at least twenty.

In one embodiment, the probe is capable of hybridizing to at least seventeen effectively contiguous nucleotides in the DNA sequence of FIG. 1 or its complement. In another embodiment, the probe comprises at least seventeen effectively contiguous nucleotides. In still a further embodiment, the probe comprises at least seventeen effectively contiguous nucleotides and is capable of hybridizing to at least seventeen effectively contiguous nucleotides in the DNA sequence of FIG. 1 or its complement. In any of these embodiments, the hybridized region of the probe and the DNA sequence of FIG. 1 or its complement, may have 90–100% complementarity.

Moreover, even if a discrete nucleotide sequence of one strain of *N. gonorrhoeae* were to exist that is useful for recognition by a polynucleotide probe, it is essential that the probe be specific for other strains of *N. gonorrhoeae* as well. Otherwise, as with the polynucleotide probe derived from the gonococcal cryptic plasmid, such nucleotide sequence by itself would be of very limited utility.

The polynucleotide probes of this invention are useful for determining the presence of *N. gonorrhoeae* nucleic acids in a sample or medium suspected of being infected with gonorrhea. Any standard method for specifically detecting double stranded nucleic acid sequences can be used. In general, the methods of this invention involve treatment of a sample or medium suspected of being infected with gonorrhea to form a single stranded target nucleotide sequence ("target sequence") from any *N. gonorrhoeae* nucleic acids that may be present in the sample or medium. The sample and at least one polynucleotide probe of the invention are then combined in an assay medium under standard conditions which allow the probe to hybridize to the target sequence present in the sample to form detectable nucleic acid complexes. The probe(s) is (are) capable of hybridizing to at least a portion of the DNA sequence of FIG. 1 or its complement.

Detection can be accomplished by directly or indirectly labeling the probe with a radioactive isotope or enzyme, for example. The labeled probe is referred to as a "conjugate". Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count. When the probe or the sample nucleic acid is bound to a support, the detection step may first involve removing the support from the medium, which is then washed free of unbound material, and then examined for the presence of the target sequence, for example, by detecting the presence of a label or a reporter group. Generally, this examination involves contacting the support with the remaining members of a signal producing system in order to produce a signal in relation to the presence of the target sequence in the sample.

In order to separate the analyte from the other components in an assay mixture containing a sample it can be desirable, and indeed preferable in some circumstances, that there is a means for immobilizing one of the components. Generally, this involves a support. The component in question can be treated to bind it to a support prior to the use in the method of the present invention. Either the target sequence or the polynucleotide probe can be immobilized. Numerous methods are known for binding nucleotide sequences to solid supports. For example see Goldkorn et al., *Nucleic Acids Research* (1986) 14:9171–9191 and the references contained therein. Frequently, the procedures for attaching a nucleotide sequence to a support involve chemical modifications of some of the nucleotides in the sequence whereby the sequence can then be attached to the support. Preferably, the bond between the support and the nucleotide sequence will be covalent, more preferably involving a linking group between the nucleotide sequence the support. For example, the support can be treated to introduce maleimide groups and the nucleotide sequence can be treated to introduce a thiol group. The thiol group is reactive with the activated olefin of the maleimide group and in such a fashion the nucleotide sequence can be covalently bound to the support. Examples of other such linking groups are cellulose derivatized with diazobenzyloxymethyl groups as described by Noyes, et al., *Cell* (1975) 5:301 and Alwine et al., *Proc. Natl. Acad. Sci. USA* (1977) 74:5350, and cellulose derivatized with o-aminophenylthioether, such as described by Seed, *Nucleic Acids Research* (1982) 10:1799.

One embodiment of this invention involves immobilization of the target sequence on a solid support such as nitrocellulose paper, cellulose paper, diazotized paper, or a nylon membrane. After the sequence is fixed on the support, the support is contacted with a suitably labeled polynucleotide probe for about ten minutes to forty-eight hours. After the above time period, the solid support is washed several times to remove unbound probe and the hybridized material is detected by autoradiography or spectroscopic methods.

Another method utilizing probes is described in U.S. Pat. No. 4,868,104, the disclosure of which is incorporated herein by reference. The method comprises combining in an assay medium the sample and first and second polynucleotide probes. Each probe is capable of hybridizing to the DNA sequence of FIG. 1 or its complement, and subsequences thereof. More specifically, each probe hybridizes to a different region of the target sequence. The first probe contains a means for rendering the first probe non-covalently polymerizable and the second probe contains means for rendering the second probe detectable. The sample and the first and second probes are combined in the assay medium under conditions for polymerizing the first probe wherein the second probe becomes bound to the polymerized first probe only when the analyte is present in the sample. A determination is then made as to whether the second probe has become bound to the polymerized first probe.

If the nucleotide sequence or the probe is not initially bound to a support, it may be desirable to bind the sequence or preferably the probe, to a support at some time during the method of the invention, preferably, prior to the detection step. Accordingly, the support and the nucleotide sequence to be bound must contain reactive groups which can provide a linkage between the support and the nucleotide sequence. The nature of the reactive groups will be such as to be compatible with the method of the present invention.

One such system is that described above where the support would contain maleimide groups and the nucleotide sequence would contain a thiol group. In another embodiment the nucleotide sequence and the support can contain complementary specific binding pair members such as biotin-avidin and the like. Thus, the method of the present invention can be run in solution and at the appropriate time the support can be introduced whereupon the complementary sbp members will bind. After the support is washed to remove unbound material, further reactions or determinations can be carried out.

In the situation where the nucleotide sequence is covalently attached to the support, it may be desirable to remove the attached sequence from the support, such as, for example, in order to amplify the sequence. In this situation it is desirable to introduce a cleavable group between the nucleotide sequence and the support. Exemplary of such cleavable groups are pyrophosphate linkages, disulfide linkages and restriction enzyme cleavage sites.

In the aforementioned examples of methods suited for use with the polynucleotide probes of this invention, standard assay conditions are sufficient. In carrying out the methods of this invention, a liquid, usually aqueous medium will be employed, usually oxygenated organic solvents from one to six, preferably one to four, carbon atoms, including alcohols, ethers, and the like. Typically, these cosolvents will be present in less than about twenty weight percent. Generally, the pH for the medium will usually be in the range of about 5 to 10, more usually in the range of about 6 to 9. Various buffers may be used to achieve the desired pH and maintain the pH during the assay. Illustrative buffers include borate, phosphate, carbonate, Tris, barbitol and the like. The particular buffer employed is not critical to this invention but in individual methods one buffer may be preferred over another.

Moderate temperatures are normally employed for carrying out the methods disclosed herein. In conducting the assay methods, the medium may be cycled between two or three temperatures or the medium may be maintained at a constant temperature. If the temperature of the medium is to be cycled, temperatures will generally range from about 10° to 100° C., more usually from about 40° to 98° C., preferably 50° to 97° C. If the medium is to be maintained at a constant temperature, the assays are usually done from about 0 to 70° C., more usually from about 15° to 50° C. The exact temperatures can be varied depending on the salt concentration, pH, solvents used, chain length and composition of the analyte.

The time period for carrying out the methods of the invention will generally be long enough to achieve hybridization. Generally, the time period for conducting the method will be from about one minute to two hours or more. When temperature cycling is employed, the time periods will be about 5 seconds to 10 minutes per cycle and any number of cycles can be used from 1 to as high as 200 or more, usually 1 to 80, frequently 10–40. As a matter of convenience it will usually be desirable to minimize the time period and the number of cycles. As a matter of convenience, it will usually be desirable to minimize the time period.

As a matter of convenience, the probe(s) employed in the present invention can be provided in a kit in packaged combination with predetermined amounts of the probe(s) for use in assaying for *N. gonorrhoeae* nucleic acids in a sample. For example, a kit useful in a method for determining the presence of *N. gonorrhoeae* nucleic acids in a sample suspected of being infected with gonorrhea can comprise in packaged combination: (1) at least one polynucleotide probe specific for *N. gonorrhoeae*, which hybridizes to the DNA sequence of FIG. 1 or its complement, or to subsequences thereof, (2) means for rendering said probe detectable, and (3) ancillary materials as required.

Where particles are employed as the label, the kit can further comprise any materials necessary to incorporate the particles into the polynucleotide probe. For example, such material can be a receptor for an organic residue bound to the probe, which receptor is conjugated to the particles.

Where an enzyme is used as the label, the materials can include an enzyme labeled sbp member, substrate for the enzyme, or precursors therefor, including any additional substrates, enzymes and cofactors and any reaction partner of the enzymic product required to provide a detectable chromophore or fluorophore, and any other members of a signal producing system.

The relative amounts of the various materials in the kits can be varied widely to provide for concentrations in solution of the materials which substantially optimize the sensitivity of the assay. In addition, the materials in the kit can be provided as dry powders, usually lyophilized, including excipients, which on dissolution will provide for a solution having the appropriate concentrations for performing the assay.

In addition to their use as detection probes the presently disclosed nucleotide sequences can be used as ligands for the sandwich capture of *N. gonorrhoeae* nucleic acids. By using two probes which hybridize to different regions of the analyte, a sandwich assay can be easily performed. One probe would comprise a means for rendering the complexes detectable. The sandwich could be formed in solution and subsequently bound to a support. Alternatively, one probe could be first bound to a support, contacted with the sample and then combined with the labeled probe.

The nucleotide sequences of this invention also find utility as primers for in vitro amplification of *N. gonorrhoeae* sequences. One method of amplification involves polymerase chain reaction (PCR) technology which uses two DNA probes which are homologous to different regions of the analyte. Only the region of the analyte between the two probes is highly amplified, and therefore can be readily isolated and characterized. This invention also pertains to a polypeptide having an amino acid sequence as set forth in FIG. 1. More specifically, this invention pertains to oligopeptides selected from that amino acid sequence. These oligopeptides are useful to raise antibodies. The antibodies will have binding affinity to the amino acid sequences against which they were raised. This invention also contemplates use of antibodies raised against peptides other than those set out in FIG. 1, but which still have binding affinity for the oligopeptides of this invention. It is expected that the antibodies of this invention will have utility in the diagnosis of gonorrhoeae infection. The oligopeptides may vary in length from five amino acids to the length of the entire sequence of FIG. 1, but as a matter of convenience will be short, usually five to twenty, preferably five to ten, most preferably about six amino acids long.

The peptides of this invention are readily synthesized by techniques well established in the art such as is set forth in Stewart et al., *Solid Phase Peptide Synthesis* (Pierce Chemical Co., Rockford Ill. 1984) and Bodansky et al., *The Practice of Peptide Synthesis* (Springer-Verlag, New York 1984), both of which are incorporated herein by reference. Typical processes that can be utilized include, without limitation, an azide process, an acid chloride process, an acid anhydride process, a mixed anhydride process, a DCC process, an active ester process, a carbodiimidazole process, an oxidation-reduction process or a DCC/additive process. In addition, the peptides of this invention can be synthesized by either solid or solution phase synthesis, and can be synthesized by a step-wise process which involves sequentially condensing amino acids one by one to the terminal amino acid or by coupling peptide fragments to the terminal amino acid.

Polyclonal antibodies are generated by repeated immunization of an animal with an immunogenic substance. Blood of the animal is collected shortly after the immunization treatment and the gamma globulin is isolated. Techniques for preparing polyclonal antisera are well established in the art and an excellent discussion is presented in Williams et al., *Methods in Immunology and Immunochemistry*, Vol. 1 (Academic Press, New York 1967), which is incorporated herein by reference.

Monoclonal antibodies can be prepared from various mammalian hosts by techniques which are well known in the art. See Kohler et al., *Nature* (1975) 256:495–497. Typically, the animals are injected with an immunogenic substance and subsequently sacrificed. Cells are taken from the animal's spleen and fused with myeloma cells, resulting in a hybrid cell or "hybridoma". Individual clones are then isolated by screening the hybridomas. These clones secrete a single antibody species to the immunogenic substance.

The peptides of this invention may be used alone in certain cases as immunogenic substances but will normally be bound to a carrier such as a natural or synthetic protein having a high molecular weight, such as are commonly used in the preparation of immunogenic substances.

EXAMPLES

The invention is demonstrated further by the following illustrative examples. Temperatures are in degrees centigrade (°C.). Parts and percentages are by weight:volume unless otherwise specified.

The following abbreviations are used in the description of the examples.

BSA—bovine serum albumin

DENHARDT'S SOLUTION—0.02% BSA, 0.02% polyvinylpyrrolidone, 0.02% Ficoll

EDTA—ethylenediaminetetraacetate

IPTG—isopropyl-β-D-thiogalactopyranoside kb—kilobase pair(s)

PCR—polymerase chain reaction

PEG—polyethylene glycol, Mol. Wt. 6000

PERT—phenol emulsion reassociation technique

SDS—sodium dodecyl sulfate

SSC—0.15 M NaCl, 0.015 M Na citrate

SSPE—80 mM NaCl, 10 mM $Na_{1.5}PO_4$, 1 mM EDTA, pH 8.0

TE—10 mM Tris-Cl, pH 8.0, 1 mM EDTA

Restriction enzymes were obtained from a variety of commercial sources and digestions were carried out in the React™ buffer system (Bethesda Research Laboratories). Agarose gel electrophoresis conditions were as set forth in Maniatis et al., *Molecular Cloning. A Laboratory Manual* (Cold Spring Harbor, Cold Spring Harbor Laboratory) pp. 150–162 (1982). Agarose gel-separated restriction fragments were purified with Geneclean™ (Bio 101). Oligodeoxynucleotides were synthesized on a Biosearch DNA Synthesizer. Kodak X-Omat AR x-ray film was used for autoradiography. When required, Cronex® Lightning Plus intensifying screens (DuPont Instruments, Wilmington, Del.) were used at −70°. In general, protocols for use of the enzymes were taken from suppliers technical literature.

Bacterial strains used in the examples set forth herein are listed in Table 1.

TABLE 1

| Bacterial strains used for DNA preparations | | |
|---|---|---|
| Strain | Number | Serotype |
| *Neisseria gonorrhoeae* | 3 | IB-03 |
| *Neisseria gonorrhoeae* | 8 | IB-04 |
| *Neisseria gonorrhoeae* | 20 | IB-01 |
| *Neisseria gonorrhoeae* | 125 | IB-02 |
| *Neisseria gonorrhoeae* | 87022192 | IA-01 |
| *Neisseria gonorrhoeae* | 87027086 | IA-01 |
| *Neisseria gonorrhoeae* | 86000866 | IA-05 |
| *Neisseria gonorrhoeae* | RR091 | IA-01 |

TABLE 1-continued

Bacterial strains used for DNA preparations

| Strain | Number | Serotype |
|---|---|---|
| Neisseria gonorrhoeae | RR153 16136 | IB-05 |
| Neisseria gonorrhoeae | RR171 16658 | IB-12 |
| Neisseria gonorrhoeae | RR199 17014 | IB-12 |
| Neisseria gonorrhoeae | RR233 17323 | IB-05 |
| Neisseria gonorrhoeae | RR264 17558 | IB-04 |
| Neisseria meningitidis | ATCC 13077 | A |
| Neisseria meningitidis | ATCC 13090 | B |
| Neisseria meningitidis | ATCC 13102 | C |
| Neisseria cinerea | ATCC 14685 | |
| Neisseria elongata | ATCC 25295 | |
| Neisseria lactamica | ATCC 23970 | |
| Neisseria mucosa | ATCC 19696 | |
| Neisseria sicca | ATCC 9913 | |
| Neisseria subflava | ATCC 14799 | |
| Branhamella catarrhalis | ATCC 8176 | |

A complete serotype listing of *N. gonorrhoeae* strains which were evaluated is shown in Table 2. Neisseria and *Branhamella catarrhalis* cultures were grown on Chocolate II Agar Plates under 5% $CO_2$ at 37°. Liquid cultures of *N. meningitidis* (ATCC 13090) were prepared in Mueller Hinton Broth (BBL), incubated at 37°, and aerated by rotation at 150 rpm.

TABLE 2

*Neisseria gonorrhoeae* strains listed by serotype

| Serotype | Number tested | Serotype | Number tested |
|---|---|---|---|
| IA-01 | 3 | IB-01 | 5 |
| IA-01,02 | 4 | IB-02 | 6 |
| IA-03 | 4 | IB-03 | 5 |
| IA-04 | 4 | IB-04 | 6 |
| IA-05 | 5 | IB-05 | 5 |
| IA-06 | 4 | IB-06 | 5 |
| IA-08 | 4 | IB-07 | 3 |
| IA-09 | 4 | IB-08 | 3 |
| IA-10 | 2 | IB-09 | 2 |
| IA-14 | 1 | IB-10 | 2 |
| IA-15 | 2 | IB-11 | 2 |
| IA-(?) | 1 | IB-12 | 3 |
| | | IB-13 | 2 |
| | | IB-14 | 2 |
| | | IB-15 | 4 |
| | | IB-16 | 3 |
| | | IB-17 | 2 |
| | | IB-18 | 3 |
| | | IB-19 | 2 |
| | | IB-20 | 2 |
| | | IB-23 | 1 |

EXAMPLE 1

Cloning of a *Neisseria gonorrhoeae*-Specific Chromosomal Sequence Through the Use of Subtractive PERT Hybridization

*N. gonorrhoeae* strain 125 DNA was isolated by lysing the cells with SDS and Proteinase K followed by extraction with phenol, chloroform and ethanol precipitation. The DNA was further purified on CsCl-ethidium bromide gradients overlayed on a cushion of 5.7 M CsCl as described by Lacy et al., *Cell* (1983) 34:343–358. *N. meningitidis* (ATCC 13090) DNA was prepared from liquid-grown cultures by lysis as described above followed by RN'ase A treatment and isopropanol precipitation.

The cloning strategy of Kunkel et al., *Proc. Natl. Acad. Sci. USA* (1985) 82:4778–782, was used to isolate *N. gonorrhoeae*-specific sequences. *N. gonorrhoeae* strain 125 DNA was digested to completion with restriction endonuclease Sau3AI. *N. meningitidis* (ATCC 13090) chromosomal DNA was sonicated to fragments primarily 1–4 kb in size. PERT hybridizations contained 100 μg of heat-denatured *N. meningitidis* DNA fragments and 1 μg of heat-denatured Sau3AI-digested *N. gonorrhoeae* DNA in 1 ml of 12 M $NaClO_4$ in 0.12M. Na phosphate, pH 6.8. Phenol (90%, vol/vol) was then added to a final concentration of 8.2% (vol/vol). The reaction was shaken at 250 rpm for 8 hours at 55°, extracted twice with chloroform to remove phenol, dialyzed against TE, ethanol precipitated and redissolved in 50–100 μl of TE.

The PERT-hybridized Sau3AI restriction fragments were ligated into pGEM-3zf(+) (Promega) that had previously been digested with BamHI and treated with bacterial alkaline phosphatase. The ligation products were used to transform XL-1 Blue competent cells according to the supplier's protocol (Stratagens). Transformants were selected by plating the cells onto LB agar plates containing 150 μg/ml ampicillin, 40 μg/ml Bluo-Gal (Gibco-BRL) and 0.2 mM IPTG. Insert-containing plasmids were identified from colonies having either a white or pale blue color.

Bacterial strains tested in dot blot hybridizations were grown on agar medium, harvested and the nucleic acids were isolated by SDS and Proteinase K lysis followed by phenol, chloroform extraction. Nucleic acid samples (approximately 100 ng) were then alkali denatured, bound to GeneScreen™ hybridization membranes and covalently coupled to the membrane by UV cross-linking.

Insert-containing plasmids were linearized by digestion with restriction endonuclease EcoRI and radioactive riboprobes were prepared using [α-$^{32}$P]CTP and SP6 Polymerase according to the supplier's protocol (Promega). See also Melton et al., *Nucleic Acids Research* (1984) 12:7035–7056. Nucleic acid dot blocks were hybridized with riboprobes as described by Amasino, *Analytical Biochemistry* (1986) 152:304–307. Blots were prehybridized in 50% (vol/vol) deionized formamide, 0.25M Na HPO , pH 7.2, 0.25M NaCl, 1 mM EDTA, 7% SDS and 10% PEG for 20–60 minutes at 42°. Riboprobe was added to a final concentration of 1×10$^6$ cpm/ml and incubation at 42° was continued for 12–16 hours. The blots were washed once for 10–15 minutes at room temperature in 2×SSC, followed by two 30 minute washes at 65° in 2×SSC, 1% SDS, and two additional 30 minute washes at 65° in 0.2×SSC, 1% SDS.

Riboprobe from a transformant containing a plasmid having the insert designated P-11 was used to hybridize to a dot blot containing nucleic acids from 10 *N. gonorrhoeae* strains, 3 *N. meningitidis* strains, 6 commensal Neisseria strains and *B. catarrhalis*. The resulting autoradiograph showed that the P-11 sequence hybridized to nine out of ten *N. gonorrhoeae* (A1-A4, A-6-A-8 and B1-B2) (C1) strains and *N. mucosa*. The specific dot blot samples that were tested are as follows:

| A1 | *N. gonorrhoeae* 125 |
|---|---|
| A2 | *N. gonorrhoeae* 87022192 |
| A3 | *N. gonorrhoeae* RR091 |
| A4 | *N. gonorrhoeae* 86000866 |
| A5 | *N. gonorrhoeae* RR153 16136 |
| A6 | *N. gonorrhoeae* RR264 17558 |
| A7 | *N. gonorrhoeae* RR233 17323 |
| A8 | *N. gonorrhoeae* RR171 16658 |

| | |
|---|---|
| B1 | *N. gonorrhoeae* RR199 17014 |
| B2 | *N. gonorrhoeae* 87027086 |
| B3 | *N. meningitidis* ATCC 13077 |
| B4 | *N. meningitidis* ATCC 13090 |
| B5 | *N. meningitidis* ATCC 13102 |
| B6 | *N. cinerea* ATCC 14685 |
| B7 | *N. elongata* ATCC 25295 |
| B8 | *N. lactamica* ATCC 23970 |
| C1 | *N. mucosa* ATCC 19696 |
| C2 | *N. subflava* ATCC 14799 |
| C3 | *N. sicca* ATCC 9913 |
| C4 | *B. catarrhalis* ATCC 8176 |

The conditions were: autoradiograph after 0.2×SSC, 1% SDS washes at 65°; and 16 hour exposure at −70° with one intensifying screen. Subsequent dot blot hybridizations showed that the P-11 riboprobe hybridized to 96 out of 96 additional *N. gonorrhoeae* strains tested.

EXAMPLE 2

P-11 Related Sequences That Lack Homology to *N. mucosa* Yet Retain Specificity for *N. gonorrhoeae*

A chromosomal DNA library of *N. gonorrhoeae* strain 125 was prepared to obtain sequences bordering the original P-11 sequence. Partially Sau3AI-digested strain 125 DNA (primarily 4–20 kb) was ligated to BamHI-digested, bacterial alkaline phosphatase-treated pGEM-3zf(+). The ligation mix was used to directly transform competent HB101 *E. coli* cells according to the supplier's protocol (Invitrogen). Colonies were lifted onto nitrocellulose filters, lysed, and the DNA was fixed essentially as described by Haas and Fleming, *Nucleic Acids Research* (1986) 14:3976. The filters were prehybridized in 50% (vol/vol) formamide, 5×Denhardt's solution, 5×SSPE, 0.1% SDS, 10% PEG, for one hour at 42°. Riboprobe was then added directly to the prehybridization mix at a final concentration of $10^6$ cpm/ml. The hybridization was allowed to proceed overnight and the filters were washed as described above for the riboprobe dot blots.

Approximately 7200 colonies were screened with the P-11 riboprobe and a total of five plasmids were identified that contained genomic sequences flanking P-11. Plasmid GC-24 (2.4 kb insert) was selected for DNA sequence analysis since it contained approximately 1 kb on either side of the P-11 region. The DNA sequence of a 2 kb region of plasmid GC-24 was determined from both strands. See Henikoff, *Gene* (1984) 28:351–359, Zhang et al., *Nucleic Acids Research* (1988) 16:1220, Biggin et al., *Proc. Natl. Acad. Sci. USA* (1983) 80:3963–3965 and Tabor and Richardson, *Proc. Natl. Acad. Sci. USA* (1987) 84:4767–4771. Analysis of the sequence data demonstrated that the region contained two long open reading frames (ORFs) of 828 and 1037 base pairs (FIG. 3). ORF 1 was truncated at its 5' end but ORF 2 contained both a translational start and stop codon.

The two open reading frames were tested for cross-hybridization to *N. mucosa* DNA. ORF 1, represented by a 763 bp BamHI-Bsu36AI fragment, and ORF 2, represented by an 820 bp Bsu36AI-SalI fragment (FIG. 2) were gel purified and random-primed labeled as described by Feinberg and Vogelstein, *Analytical Biochemistry* (1983) 132:6–13. Each probe was then checked for specificity with the dot blots described in Example 1. The dot blots were prehybridized in 5×Denhardt's solution, 5×SSPE, 0.1% SDS and 10 μg/ml sheared, heat-denatured herring testes DNA. After at least one hour at 65°, heat-denatured probe was added directly to the prehybridization solution to a final concentration of 1×–2×$10^6$ cpm/ml. The hybridization was continued overnight at 65° and the blots were washed under increasingly stringent conditions. The ORF 1 probe did not hybridize to *N. mucosa* DNA after a high stringency wash (0.1×SSC, 1% SDS, 2×30 minutes, 65°), whereas the ORF 2 probe did. Both probes recognized 105 of 106 *N. gonorrhoeae* stains and neither probe hybridized to *N. meningitidis* (3 different serotypes), six non-pathogenic Neisseria strains, nor *B. catarrhalis*.

EXAMPLE 3

ORF 1 was divided into three equal regions, each being defined as an approximately 300 bp PCR product. PCR products were generated under conditions suggested by Perkin-Elmer Cetus. See also Saiki, et al., *Science* (1988) 239:487–491. PCR-1 consisted of bases 1–276 (SEQ ID NO:4), PCR-2 consisted of bases 262–564 (SEQ ID NO:5), and PCR-3 consisted of bases 551–850 (SEQ ID NO:6) as diagrammed in FIG. 1. Each PCR product was gel purified and random-prime labeled as described above. Each PCR product was hybridized to both dot blots and chromosomal restriction digests in dried agarose gels.

Dot blot hybridizations were done as described in Example 2 and washed as described below. Dried-gel nucleic acid hybridizations were performed as described by Miyada and Wallace, *Methods in Enzymology* (1987) 154:94–107. Dried gels were hybridized with random-primed probes in 5×SSPE, 0.1% SDS, containing both 10 μg/ml sonicated, denatured *E. coli* DNA, and 2×$10^6$ cpm/ml of $^{32}$P-labeled probe. Following overnight hybridization at 65°, gels were washed 10–15 minutes at room temperature in 2×SSC. They were then washed under conditions of increasing stringency. Each wash condition consisted of two 30 minute washes at 65°. In order of increasing stringency, the wash buffers were 2×SSC, 1×SSC, 0.5×SSC, and 0.2× SSC. All of the washes also contained 0.1% SDS. In both types of hybridizations, cross-hybridization to *N. mucosa* DNA disappeared after a stringent wash (0.2× SSC). An example using samples in a dried agarose gel is shown in FIG. 4, where:

| | |
|---|---|
| Lane 1 | GC-24 (4 ng) |
| Lane 2 | *N. gonorrhoeae* 125 |
| Lane 3 | *N. gonorrhoeae* 3 |
| Lane 4 | *N. gonorrhoeae* 8 |
| Lane 5 | *N. gonorrhoeae* 20 |
| Lane 6 | *N. mucosa* |
| Lane 7 | GC-24 (8 ng) |

After hybridization, the gel was washed at room temperature in 2×SSC for 15 minutes, followed by two 30 minute washes in 2×SSC, 0.1% SDS at 65° C., and two additional 30 minute washes in 1×SSC, 0.1% SDS at 65°. The gel was then exposed for 2 hours at −70° with two intensifying screens. In this single exposure, Lanes 1–7 indicated hybridization the first exposure, the gel was given two 30 minute washes in 0.2×SSC, 0.1% SDS at 65° and re-exposed as before. In this re-exposure, Lane 6 (*N. mucosa*) no longer indicated hybridization.

EXAMPLE 4

Specificity of an Oligonuleotide Probe Derived from OTF-1

An oligodeoxyribonucleotide, P-11 20-mer a 20-mer from the P-11 sequence (5'-ACAGCATTACCAATCTGGCG-3'

(SEQ ID NO:3), bases 738–757, complementary strand, FIG. 1), was labeled with $^{32}$P via a kinase reaction as described by Miyada and Wallace. It was then used as a probe in dot blot hybridizations as described in Example 3, except that the hybridization temperature was 50°. After the hybridization the blots were given two 15 minute washes in 6×SSC at room temperature and an additional wash for 1 minute at 52.5° in 6×SSC. The resulting autoradiograph showed that the 20-mer did not hybridize to either *N. mucosa*, 6 other non-pathogenic Neisseria, *B. catarrhalis* or 3 *N. meningitidis* strains. Other dot blots showed that the 20-mer hybridized to 105 out of 106 *N. gonorrhoeae* strains under the above conditions.

The above discussion includes certain theories as to mechanisms involved in the present invention. These theories should not be construed to limit the present invention in any way, since it has been demonstrated that the present invention achieves the results described.

The invention has been described in detail with particular reference to the above embodiments. It will be understood, however, that variations and modifications can be effected within the spirit and scope of the invention.

What is claimed is:

1. A support having bound thereto at least one polynucleotide probe specific for *N. gonorrhoeae* which is 90–100% complementary to at least seventeen contiguous nucleotides of SEQ ID NO:1 or its complement.

* * * * *